US009233251B2

(12) United States Patent
Rajan et al.

(10) Patent No.: US 9,233,251 B2
(45) Date of Patent: Jan. 12, 2016

(54) BI-ATRIAL SYNCHRONIZED LEFT VENTRICULAR CARDIAC PACING

(71) Applicant: Medtronic, Inc., Minneapolis, MN (US)

(72) Inventors: Vinayakrishnan Rajan, Maastricht (NL); Berthold Stegemann, Bonn (DE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/157,161

(22) Filed: Jan. 16, 2014

(65) Prior Publication Data
US 2015/0196760 A1 Jul. 16, 2015

(51) Int. Cl.
*A61N 1/00* (2006.01)
*A61N 1/368* (2006.01)

(52) U.S. Cl.
CPC ............. *A61N 1/3682* (2013.01); *A61N 1/368* (2013.01); *A61N 1/3684* (2013.01)

(58) Field of Classification Search
USPC ........................................ 607/9, 18
See application file for complete search history.

(56) References Cited

U.S. PATENT DOCUMENTS

| | | | |
|---|---|---|---|
| 5,902,324 A | 5/1999 | Thompson | |
| 6,070,101 A | 5/2000 | Struble | |
| 6,122,545 A | 9/2000 | Struble et al. | |
| 6,466,824 B1 | 10/2002 | Struble | |
| 6,477,420 B1 | 11/2002 | Struble et al. | |
| 6,574,506 B2 | 6/2003 | Kramer et al. | |
| 6,751,504 B2 | 6/2004 | Fishler | |
| 6,754,529 B2 | 6/2004 | Struble | |
| 6,882,882 B2 | 4/2005 | Struble | |
| 7,058,443 B2 | 6/2006 | Struble | |
| 7,389,141 B2 | 6/2008 | Hall | |
| 7,412,286 B2 | 8/2008 | Busch | |
| 7,715,917 B2 | 5/2010 | Chinchoy | |
| 2003/0208238 A1 | 11/2003 | Weinberg et al. | |
| 2005/0137630 A1 | 6/2005 | Ding | |
| 2005/0137634 A1 | 6/2005 | Hall et al. | |
| 2006/0041279 A1 | 2/2006 | Yu | |
| 2006/0047319 A1 | 3/2006 | Bruhns et al. | |
| 2009/0299423 A1 | 12/2009 | Min | |
| 2010/0145405 A1* | 6/2010 | Min et al. | 607/25 |
| 2012/0109247 A1 | 5/2012 | Rajan et al. | |

FOREIGN PATENT DOCUMENTS

WO 0024457 A1 5/2000

OTHER PUBLICATIONS

Daubert, JC, et al. "Intra- and Interatrial Conduction Delay: Implications for Cardiac Pacing" PACE 2004: 27; 507-525.
(PCT/US2015/011505) PCT Notification of Transmittal of the International Search Report and the Written Opinion of the International Searching Authority.

* cited by examiner

*Primary Examiner* — Nicole F Lavert
(74) *Attorney, Agent, or Firm* — Carol F. Barry

(57) ABSTRACT

A medical device performs a method for controlling a cardiac pacing therapy. The device determines an inter-atrial conduction time (IACT) and compares the IACT to a threshold. A controller included in the device sets a pacing interval for controlling delivery of pacing pulses to a ventricle to a first ventricular pacing interval that expires after the IACT in response to the IACT being less than the threshold and sets the pacing interval to a second ventricular pacing interval that expires before the IACT in response to the IACT being greater than the threshold.

22 Claims, 9 Drawing Sheets

BI-ATRIAL SYNCHRONIZED LEFT VENTRICULAR CARDIAC PACING

TECHNICAL FIELD

The disclosure relates to an implantable medical device and method for performing bi-atrial synchronized cardiac pacing.

BACKGROUND

Cardiac resynchronization therapy (CRT) is a treatment for heart failure patients in which one or more heart chambers are electrically stimulated (paced) to restore or improve heart chamber synchrony. Improved heart chamber synchrony is expected to improve hemodynamic performance of the heart, such as assessed by ventricular pressure and the rate of change in ventricular pressure or other hemodynamic parameters, thereby alleviating symptoms of heart failure. Achieving a positive clinical benefit from CRT is dependent on several therapy control parameters, such as the atrio-ventricular (AV) delay, inter-ventricular (VV) delay and pacing site(s). The AV delay controls the timing of ventricular pacing pulses relative to an atrial depolarization, intrinsic or paced. The VV delay controls the timing of a pacing pulse in one ventricle relative to a paced or intrinsic sensed event in the other ventricle. Pacing may be delivered in the right ventricle and/or the left ventricle to restore ventricular synchrony.

Atrial conduction disorders are common in heart failure. When atrial-ventricular timing is not optimal, the atrial contribution to ventricular filling can be diminished, which can reduce ventricular ejection and hemodynamic performance. Implantable devices and associated methods are needed for delivering CRT in a manner that reduces risks of atrial conduction disorders.

SUMMARY

In general, the disclosure is directed towards a medical device system and automated method for controlling a cardiac pacing therapy by determining an inter-atrial conduction time (IACT) and comparing the IACT to a threshold. A pacing interval for controlling delivery of pacing pulses to a ventricle is set to a first ventricular pacing interval that expires after the IACT in response to the IACT being less than the threshold and sets the pacing interval to a second ventricular pacing interval that expires before the IACT in response to the IACT being greater than the threshold.

In another embodiment, a non-transitory computer-readable medium stores instructions that cause a medical device system to perform a method that includes determining an inter-atrial conduction time (IACT) and comparing the IACT to a threshold. A pacing interval for controlling delivery of pacing pulses to a ventricle is set to a first ventricular pacing interval that expires after the IACT in response to the IACT being less than the threshold and to a second ventricular pacing interval that expires before the IACT in response to the IACT being greater than the threshold.

Other embodiments and aspects of a system and method for controlling a cardiac pacing therapy are described herein. The details of one or more aspects of the disclosure are set forth in the accompanying drawings and the description below. Other features, objects, and advantages will be apparent from the description and drawings, and from the claims.

DETAILED DESCRIPTION

Figure 1:
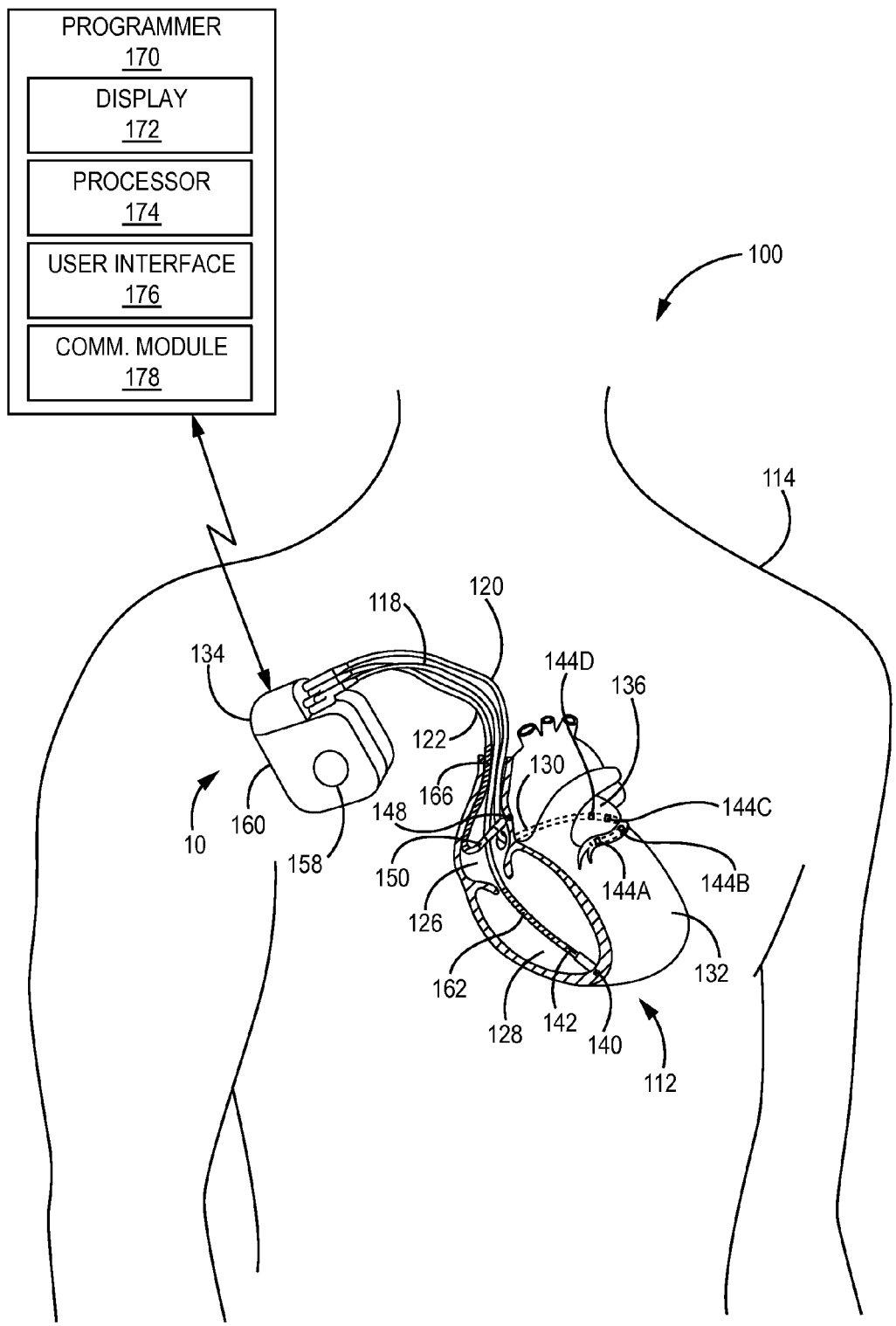
FIG. 1 is a schematic diagram of one embodiment of an implantable medical device (IMD) system in which techniques disclosed herein may be implemented to provide therapy to a heart of a patient.

FIG. 1 is a schematic diagram of one embodiment of an implantable medical device (IMD) system 100 in which techniques disclosed herein may be implemented to provide therapy to heart 112 of patient 114. System 100 is configured to sense cardiac electrical signals and deliver cardiac pacing pulses to achieve cardiac resynchronization with bi-atrial synchronization.

System 100 includes IMD 10 coupled to leads 118, 120, and 122 which carry multiple electrodes. IMD 10 is configured for bidirectional communication with programmer 170. IMD 10 is an implantable pacemaker or implantable cardioverter defibrillator (ICD) that delivers electrical signals to heart 112 via electrodes coupled to one or more of leads 118, 120, and 122 for pacing, cardioverting and defibrillating the heart 112. IMD 10 is capable of delivering pacing in one or more heart chambers, and in the embodiment shown, is configured for multi-chamber pacing and sensing in the right atrium (RA) 126, the left atrium (LA) 136, the right ventricle (RV) 128, and the left ventricle (LV) 132 using leads 118, 120 and 122.

IMD 10 senses cardiac electrogram (EGM) signals produced by the depolarization of myocardial cells. EGM signals may arise from intrinsic depolarization wavefronts produced by the sinoatrial node and conducted through the myocardial tissue. EGM signals may also arise from evoked depolarization wavefronts produced by pacing pulses and conducted through the myocardium. Sensed events in a given heart chamber may therefore be an intrinsic event that arises without delivery of a pacing pulse and evoked events that arise due to a pacing pulse delivered in the heart chamber or another heart chamber. Unless otherwise specified, as used herein a sensed event refers to an intrinsic event.

IMD 10 delivers RV pacing pulses and senses RV EGM using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144A and 144B carried by a multipolar coronary sinus lead 120, extending through the RA 126 and into a cardiac vein 130 via the coronary sinus.

In the example shown, coronary sinus lead 120 is a quadripolar lead carrying electrodes 144C and 144D for positioning along the left atrium (LA) 136 for sensing left atrial (LA) EGM signals and delivering LA pacing pulses. CS lead 120 may include at least two electrodes to enable LA unipolar pacing and LV unipolar pacing. Alternatively, CS lead 120 is provided with at least four electrodes to enable bipolar sensing and pacing of both the LA 136 and the LV 138. For example CS lead 120 may include six electrodes to position four electrodes along the LV 132 and two electrodes along the LA 136 to allow multiple vectors and pacing sites to be selected from for pacing the LV 132 and bipolar pacing of the LA 136. In other embodiments, a separate transvenous or epicardial lead could be provided for positioning electrodes along the LA 136.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect tachyarrhythmias of heart 112, such as fibrillation of ventricles 128 and 132, by sensing EGM signals and deliver high voltage cardioversion or defibrillation therapy to heart 112 in the form of electrical shock pulses. Pacing and sensing of the cardiac chambers is typically achieved using the pace/sense electrodes 140, 142, 144A, 144B, 144C, 144D (collectively 144), 148 and 150, however in some embodiments coil electrodes 162 and/or 166 may be used in sensing and/or pacing electrode vectors.

While IMD 10 is shown in a right pectoral implant position in FIG. 1, a more typical implant position, particularly when IMD 10 is embodied as an ICD, is a left pectoral implant position. In other embodiments, IMD 10 may be implanted in an abdominal location.

IMD 10 includes internal circuitry for performing the functions attributed to IMD 10 throughout this disclosure. Housing 160 encloses the internal circuitry. The housing 160 or portions thereof may be configured as an active electrode 158 for use in cardioversion/defibrillation shock delivery or used as an indifferent electrode for unipolar pacing or sensing configurations with any electrodes carried by leads 118, 120 and 122. IMD 10 includes a connector block 134 having connector bores for receiving proximal lead connectors of leads 118, 120 and 122. Electrical connection of electrodes carried by leads 118, 120 and 122 and IMD internal circuitry is achieved via conductors extending through leads 118, 120 and 122 and various connectors and electrical feedthroughs included in connector block 134.

IMD 10 is configured for delivering CRT by delivering pacing pulses in one or both ventricles 128 and 132 for controlling and improving ventricular synchrony. IMD 10 may deliver RA pacing when the intrinsic heart rhythm is insufficient. As disclosed herein, IMD 10 may deliver LA pacing to improve atrial synchrony. In some embodiments, LA and LV sensing and pacing is performed using CS lead 120 and RA lead 122 and RV lead 120 are not present. In this example, CRT is provided using a single lead advanced in the coronary sinus to position electrodes along the LA and the LV to enable LA and LV pacing.

LA 136 may be paced to restore atrial synchrony using at least one electrode 144 on multipolar lead 120. LA pacing is controlled to reduce conduction delays between the RA 126 and the LA 136 while avoiding overdrive pacing of the atria. The underlying intrinsic heart rate, driven by the sinoatrial (SA) node is maintained by not pacing the RA 126 and adjusting an inter-atrial pacing interval (AAI) to mitigate an inter-atrial conduction disorder while allowing the intrinsic rate to prevail and optimizing atrial-ventricular (AV) timing for optimal cardiac performance.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device used in a hospital or clinic. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD.

Examples of communication techniques used by system 100 for programming IMD 10 and retrieving data therefrom include low frequency or radiofrequency (RF) telemetry, which may be an RF link established via Bluetooth, WiFi, or MICS for example. Programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote monitoring and management of patient 114 using the techniques described herein. Remote patient management systems, such as CARELINK® available from Medtronic, Inc. Minneapolis, Minn., may be configured to utilize the presently disclosed techniques to enable a clinician to review pacing intervals and cardiac signal data, programmed therapy parameters and authorize remote programming of IMD 10.

Figure 2:
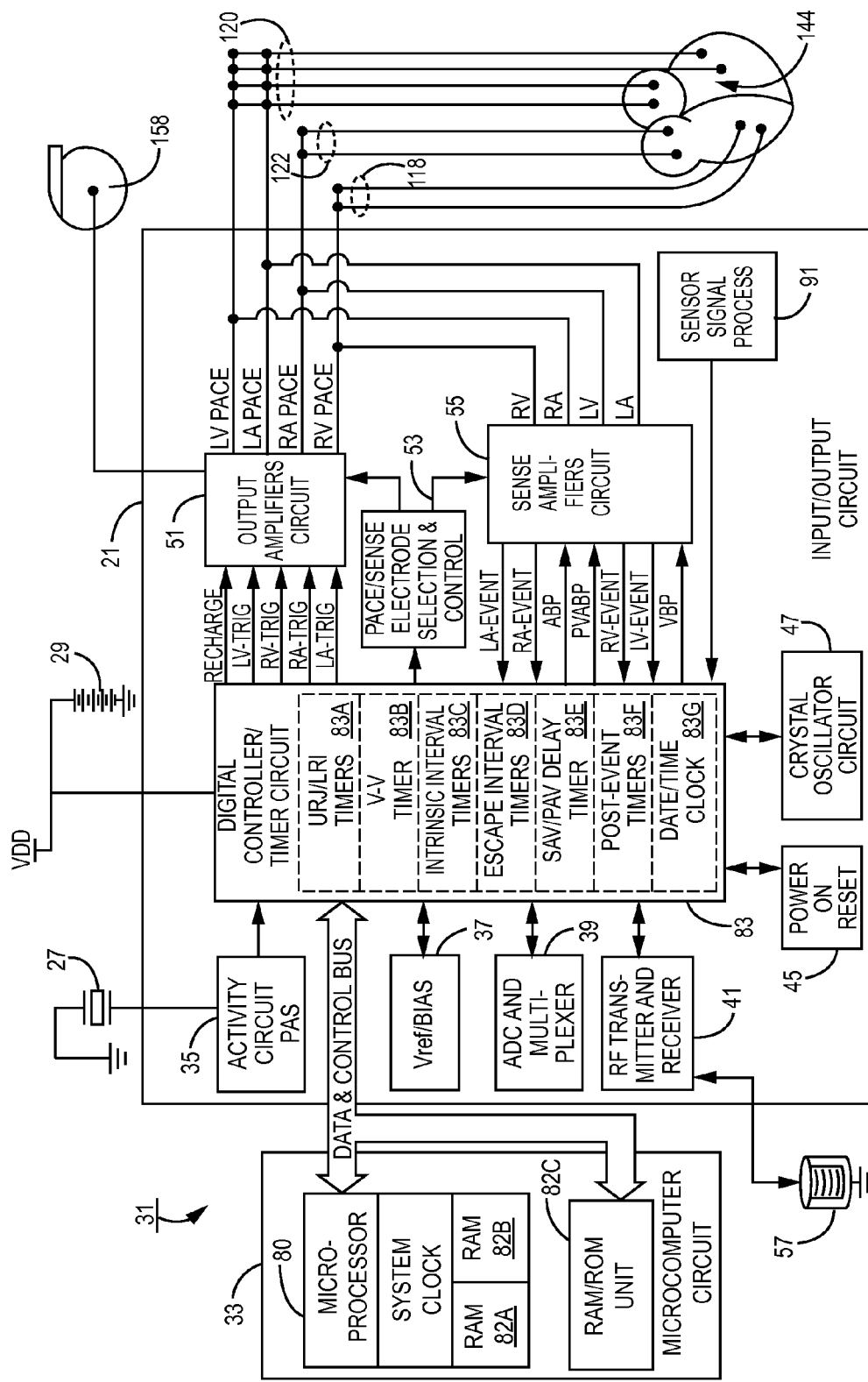
FIG. 2 is a functional block diagram of circuitry included in the IMD of FIG. 1 according to one illustrative embodiment.

FIG. 2 is a functional block diagram of circuitry included in IMD 10 according to one illustrative embodiment. FIG. 2 depicts bipolar RA lead 122, bipolar RV lead 118, and quadripolar CS lead 120 coupled with an implantable pulse generator (IPG) circuit 31 having programmable modes and parameters that may be included in a DDD/R type of cardiac pacemaker. The IPG circuit 31 is illustrated in a functional block diagram divided generally into a microcomputer 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below. The sensor signal processing circuit 91 is coupled to the digital controller/timing circuit 83 and to microcomputer 33 via a data and control bus for use in controlling IMD functions.

Crystal oscillator circuit 47 provides the basic timing clock for the pacing circuit 21, while battery 29 provides power. Power-on-reset circuit 45 responds to initial connection of the circuit to the battery for defining an initial operating condition and similarly, resets the operative state of the device in response to detection of a low battery condition. Voltage reference and bias circuit 37 generates stable voltage reference and currents for the analog circuits within the pacing circuit 21, while analog to digital converter (ADC) and multiplexer circuit 39 digitizes analog signals to provide real time telemetry of cardiac signals, received from sense amplifiers circuit 55, for uplink transmission via RF transmitter and receiver circuit 41. Digitally converted signals from sense amplifiers circuit 55 and/or sensor signal processor 91 may also be used by microcomputer 33 for controlling digital controller/timer circuit 83 according to programmed therapy and/or signal monitoring modes of operation.

The sense amplifiers circuit 55 contains sense amplifiers for atrial and ventricular sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers 55 are typically uncoupled from the sense electrodes during blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 158 from the inputs of the RA sense amplifier, LA sense amplifier, RV sense amplifier and LV sense amplifier during various blanking periods as described below. The sense amplifiers circuit 55 also includes switching circuits for coupling selected sense electrode lead conductors and the IND-CAN electrode 158 to the RA sense amplifier, LA sense amplifier, RV sense amplifier and LV sense amplifier. Pace/sense electrode selection and control circuit 53 selects conductors and associated sense electrode pairs to be coupled with the atrial and ventricular sense amplifiers within the sense amplifiers circuit 55 for accomplishing RA, LA, RV and LV sensing along desired unipolar and/or bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier result in a LA-EVENT signal that is communicated to the digital controller/timer circuit 83. Ventricular depolarizations or R-waves in the RV-SENSE signal that are sensed by a ventricular sense amplifier result in an RV-EVENT signal that is communicated to the digital controller/timer circuit 83. Similarly, ventricular depolarizations or R-waves in the LV-SENSE signal that are sensed by a ventricular sense amplifier result in an LV-EVENT signal that is communicated to the digital controller/timer circuit 83. The RV-EVENT, LV-EVENT, RA-EVENT and LA-EVENT signals may be refractory or non-refractory according to various refractory sensing intervals as described below, and can inadvertently be triggered by electrical noise signals or aberrantly conducted depolarization waves rather than true R-waves or P-waves. As discussed above, a sensed event may be an intrinsic event arising from the cardiac tissue itself when no pacing pulse is delivered or a pacing-evoked event that has caused depolarization of a heart chamber. For example, an evoked response to a pacing pulse delivered in the RA may be conducted to the RV and sensed as an R-wave but is not an intrinsic R-wave since it arose from the pacing pulse in the RA.

Microcomputer 33 contains a microprocessor 80 and associated system clock and on-processor RAM and ROM chips 82A and 82B, respectively. In addition, microcomputer circuit 33 may include a separate RAM/ROM chip 82C to provide additional memory capacity. Microprocessor 80 normally operates in a reduced power consumption mode and is interrupt driven in some embodiments. In such instances, microprocessor 80 is awakened in response to defined interrupt events, which may include RA-TRIG, LA-TRIG, RV-TRIG, LV-TRIG signals generated by timers in digital timer/controller circuit 83. The RA-TRIG, LA-TRIG, RV-TRIG, and LV-TRIG signals are generated for triggering pacing pulses by output amplifiers circuit 51 upon the expiration of various pacing timing escape intervals before receiving a respective RA-EVENT, LA-EVENT, RV-EVENT, or LV-EVENT signal generated by sense amplifiers circuit 55 upon a sensing threshold crossing of an RA, LA, RV, or LV EGM signal, among others.

The specific values of various intervals and delays timed out by digital controller/timer circuit 83 are controlled by the microcomputer circuit 33 by way of the data and control bus based upon programmed-in therapy control parameter values and operating modes. In addition, if programmed to operate as a rate responsive pacemaker, a timed interrupt, e.g., every cycle or every two seconds, may be provided in order to allow the microprocessor to analyze activity sensor data and update the basic A-A, V-A, or V-V escape intervals used to control pacing pulse delivery in instances that an intrinsic depolarization is not sensed in a respective cardiac chamber, as applicable. In addition, the microprocessor 80 may also serve to define variable, operative AV delay intervals and the energy, e.g. pulse amplitude and pulse width, of each pulse delivered.

Digital controller/timer circuit 83 operates under the general control of the microcomputer 33 to control timing and other functions within the pacing circuit 31 and includes a set of timing and associated logic circuits, not necessarily limited to the certain ones depicted. The depicted timing circuits include URI/LRI timers 83A for timing an upper rate limit interval and a lower rate limit interval for delivering pacing to control the heart rate within the rate limits, a V-V delay timer 83B for controlling a time interval between a ventricular paced or sensed event in ventricle and the time of a paced event in the other ventricle, intrinsic interval timers 83C for timing elapsed V-EVENT to V-EVENT intervals or V-EVENT to A-EVENT intervals or the A-V conduction interval, escape interval timers 83D for timing A-A, V-A, and/or V-V pacing escape intervals, an AV interval timer 83E for timing the RA-LVp delay (or RA-RVp delay) from a preceding RA-EVENT or A-TRIG signal, a post-ventricular timer 83F for timing post-ventricular time periods, and a date/time clock 83G.

The AV interval timer 83E is loaded with an appropriate delay interval for one ventricular chamber (e.g., either a RA-RVp delay or a RA-LVp delay as desired) to time-out starting from a preceding RA-PACE or sensed RA-EVENT. In some example, AV interval timer 83E times out a delay between a LA-PACE or LA-EVENT and a ventricular chamber pacing pulse (RV or LV). The interval timer 83E triggers pacing pulse delivery upon timing out without any intervening intrinsic sensed event, and can be based on one or more prior cardiac cycles (or from a data set empirically derived for a given patient).

The post-event timer 83F times out various refractory and blanking intervals that are used to control sensing of events associated with intrinsic depolarizations of the heart chambers. Examples of post-ventricular time periods timed by timers 83F may include post-ventricular time periods following an RV-EVENT, LV-EVENT or an RV-TRIG or LV-TRIG and post-atrial time periods following an RA-EVENT, LA-EVENT or RA-TRIG or LA-TRIG. The durations of the post-event time periods may also be selected as programmable parameters stored in the microcomputer 33. The post-ventricular time periods may include a post-ventricular atrial refractory period (PVARP), a ventricular blanking period (VBP), a post-ventricular atrial blanking period (PVABP) and a ventricular refractory period (VRP) although other periods can be suitably defined depending, at least in part, on the operative circuitry employed in the IPG circuit 31. The post-atrial time periods include an atrial refractory period (ARP), a post-atrial ventricular blanking period (PAVBP), and an atrial blanking period (ABP). Generally, during an atrial or ventricular refractory period a sensed A-EVENT or V-EVENT, respectively, is ignored for the purpose of resetting escape intervals but may be counted for other purposes such as determining a heart rate. During an atrial or ventricular blanking period, sensing of an A-EVENT or V-EVENT from a respective EGM signal is typically disabled.

The starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with a sensor based escape interval established in response to rate control parameters and/or with the intrinsic atrial rate.

The output amplifiers circuit 51 contains a RA pace pulse generator, a LA pace pulse generator, a RV pace pulse generator, and a LV pace pulse generator. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E. If biventricular pacing is delivered, a subsequent RV-TRIG (in the case of LV pre-excitation) or LV-TRIG (in the case of RV pre-excitation) is produced upon expiration of the V-V delay timer 83B to pace the second ventricle. Digital controller/timer circuit 83 generates an RA-TRIG signal that triggers output of an RA-PACE pulse at the end of the V-A escape interval timed by escape interval timers 83D. A LA-TRIG signal that triggers output of an LA-PACE pulse is produced at the end of an AA interval. Alternatively an LA-TRIG signal may be produced at the end of V-A escape interval.

The output amplifiers circuit 51 includes switching circuits for coupling selected pace electrode pairs from among the lead conductors and the housing electrode 158 to the RA pace pulse generator and LA pace pulse generator, RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing. Furthermore, pace/sense electrode pair selection and control circuit 53 selects pacing vectors for delivering pulses in the LA and the LV from the quadripolar lead 120 by selecting a respective bipolar or unipolar pacing vector including at least one of electrodes 144.

If IMD 10 is programmed to a rate responsive mode, the signals output by one or more physiologic sensor are employed as a rate control parameter (RCP) to derive a physiologic escape interval used for timing the delivery of pacing pulses. For example, the escape interval is adjusted proportionally to the patient's activity level developed in the patient activity sensor (PAS) circuit 35. The patient activity sensor 27 is coupled to the IPG housing and may take the form of a piezoelectric crystal transducer. The activity sensor output signal is processed and used as the RCP in some examples. Activity sensor 27 generates electrical signals in response to sensed physical activity that are processed by activity circuit 35 and provided to digital controller/timer circuit 83. The illustrative embodiments described herein may also be practiced in non-rate responsive pacemakers.

Data transmission to and from the external programmer 170 is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, cardiac electrogram (EGM) histograms and other events, as well as real time EGM signals of atrial and/or ventricular electrical activity and marker channel data indicating the occurrence of sensed intrinsic depolarizations and pacing pulse delivery in the atrium and ventricles. Real-time and/or stored signals received by other physiological signals including sensor 27 or other sensors listed herein that may be coupled to sensor signal processing circuit 92 and/or data derived from such signals may also be transmitted by transceiver 41.

In one embodiment, microprocessor 80 is a custom microprocessor adapted to fetch and execute instructions stored in RAM/ROM unit 82. It is contemplated, however, that other implementations may be suitable to practice the present invention. For example, an off-the-shelf, commercially available microprocessor or microcontroller, or custom application-specific, hardwired logic, or state-machine type circuit or combinations thereof may perform the functions of microprocessor 80.

The techniques described in this disclosure, including those attributed to the IMD 10 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry or state machines, as well as any combinations of such components, embodied in IMD 10, programmer 170, such as a physician or patient programmer, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as circuits, modules or units is intended to highlight different functional aspects and does not necessarily imply that such circuits, modules or units must be realized by separate hardware or software components. Rather, functionality associated with one or more circuits, modules or units may be performed by separate hardware or software components, or integrated within common or separate hardware or software components.

When implemented in software, the functionality ascribed to the systems, devices and techniques described in this disclosure may be embodied as non-transitory instructions stored on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Figure 3:
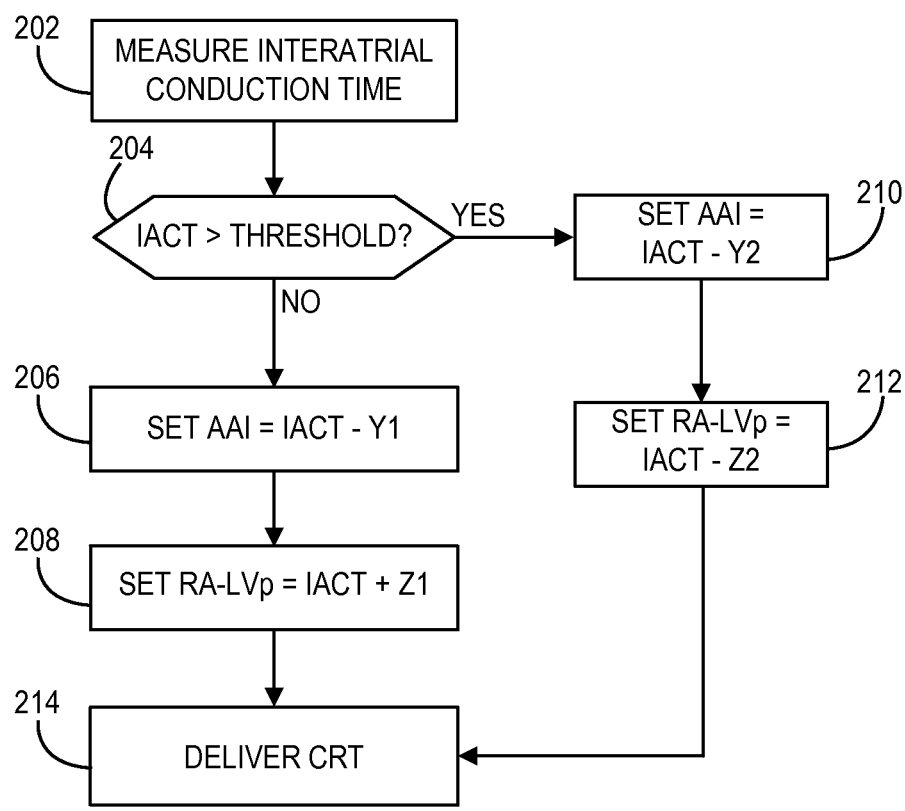
FIG. 3 is a flow chart of a method for delivering bi-atrial synchronized CRT.

FIG. 3 is a flow chart 200 of a method for delivering bi-atrial synchronized CRT. At block 202 an inter-atrial conduction time is measured (IACT). Numerous methods may be used to determine the IACT. In the IMD 10 shown in FIG. 1, the time between an intrinsic RA sensed event and an intrinsic LA sensed event can be measured from a RA EGM signal sensed using RA electrodes 148 and 150 and a LA EGM signal sensed using electrodes 144C and 144D, respectively. If RA lead 122 is not present, the electrodes 144C and 144D positioned along the LA can be used alone for determining the IACT. For example, the LA atrial EGM signal is sensed and the P-wave width is determined as a measurement of the IACT. In other examples, the IACT may be determined as the width of a far-field P-wave sensed on a ventricular EGM signal, which may be sensed using either RV electrodes 140 and 142 or LV electrodes 144A and 144B. An IACT may be measured as the time from a RA pace event, also denoted herein as "RAp," or from an intrinsic RA sense event, also denoted herein as "RAs," to the immediately following LA sense event, also denoted herein as "LAs". The IACT may be measured as the P-wave width or far-field P-wave width, following a RA pacing pulse or in the absence of pacing.

At decision block 204, the IACT is compared to a predetermined threshold established to distinguish between a normal IACT and an atrial conduction disorder. For example, an IACT less than approximately 100 ms may be considered normal conduction An IACT greater than approximately 100 ms is evidence of an atrial conduction disorder causing an abnormal delay between RA and LA depolarization. A later depolarization of the LA resulting in later contraction of the LA relative to the RA may result in contraction of the LV against a still-contracting LA and diminish the LA active filling contribution to the LV.

If the IACT is less than the threshold, a RA-LA pacing interval, also referred to herein as the "AA Interval" (AAI), may be set at block 206 to an interval less than the IACT, for example IACT−Y1. Y1 may be on the order of 10 to 80 ms, for example, and may depend on the IACT. LA pacing may be desired in some patients, even when a conduction delay is not present, to reduce the likelihood of atrial arrhythmias e.g. in patient's experiencing episodes of atrial fibrillation or to prevent refractory atrial tachycardia, or when a short AV interval is desired, e.g. for optimal pacing therapy in patients with Hypertrophic Obstructive Cardiomyopathy (HOCM).

A pacing timing interval for controlling LV pacing is set at block 208 to be longer than the measured IACT. In one example, an RA-LVp interval is set as the measured IACT plus a constant, Z1. The LV pacing pulses are delivered following a sensed or paced RA event at a time interval equal to the IACT plus Z1 ms to allow for complete LA contraction prior to LV contraction. In other examples, Z1 may be a variable that depends on the value of the IACT.

If the IACT is greater than the threshold, as determined at decision block 204, the AAI is set to a value less than the IACT at block 210, e.g. IACT minus Y2 where Y2 is greater than Y1. If abnormal AA conduction is identified, the AAI interval is shortened by a larger constant Y2 to correct the long IACT. Y2 may be a variable depending on the value of IACT.

In this case, the RA-LVp interval is set to an interval shorter than the IACT at block 212, i.e. IACT−Z2. The value of Z2 may be a constant or depend on the IACT. When an atrial conduction delay is evidenced by a long IACT, the RA-LVp interval is set shorter than the long IACT. When atrial conduction is normal based on the IACT, the RA-LVp interval is set longer than the IACT. The RA-LVp interval is an escape interval that may be restarted upon an intrinsic RA sense event (P-wave) or a RA pacing pulse or distinct RAp-LAp and RAs-LAp intervals may be set. CRT is delivered at block 214 using the automatically adjusted timing intervals set based upon the IACT measurement.

It is recognized that a RA-RVp interval may be set in addition to the RA-LVp interval. When AV nodal conduction is intact, intrinsic conduction between the RA and RV may be more beneficial to the patient than RV pacing. However, when AV conduction is blocked, an RA-RVp interval may be set. Alternatively, a VV interval may be set to pace the RV relative to the LV being paced at an RA-LVp interval set as described above.

The method shown in FIG. 3 may be performed using the multi-polar CS lead 120 shown in FIG. 1 without requiring an RV lead 118. In one example, the IACT is measured as the P-wave width sensed on electrodes 144C and 144D. An AAI is set based on the IACT, and a RA-LVp interval is set based on the IACT as described above. The LA and the LV are paced using the CS lead 120 and the RA lead 122 is used for sensing RA events (P-waves) and pacing the RA if the intrinsic rate falls below a programmed pacing rate.

Figure 4:
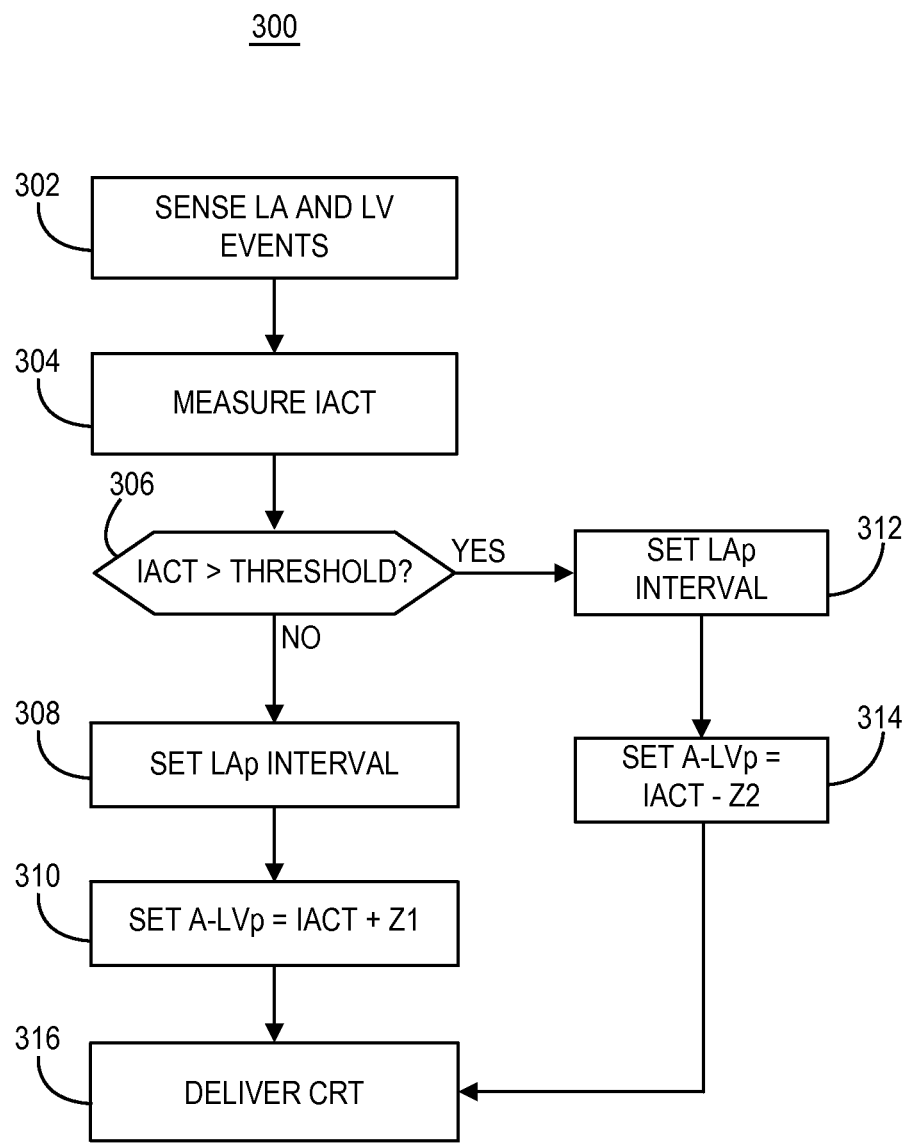
FIG. 4 is a flow chart of a method for delivering a pacing therapy using only a multi-polar coronary sinus lead, for example as shown in FIG. 1.

FIG. 4 is a flow chart 300 of a method for delivering a pacing therapy using only multi-polar CS lead 120 shown in FIG. 1. At block 302, LA and LV events are sensed using electrodes 144. The microprocessor 80 determines an intrinsic IACT from the sensed LA EGM and/or LV EGM signals at block 304 by measuring the P-wave width or the far-field P-wave width, respectively. If the IACT is normal, i.e. equal to or less than a predetermined threshold, as determined at block 306, a LA pacing interval (LAp interval) may be set at block 308 to reduce the likelihood of atrial tachyarrhythmias and/or enable pacing at relatively short AV intervals. The LA pacing interval may be an AAI started at the onset of the far-field P-wave sensed from the LV EGM signal. The LA pacing interval may alternatively be a VA interval set to be slightly longer than the time from an LV pace or LV sense event to the subsequently sensed far-field P-wave onset.

An A-LVp interval is set at block 310 at an interval greater than the measured IACT. The A-LVp interval may be an interval started at the onset of the far-field P-wave as a substitute interval for an RA-LVp interval. Alternatively, the A-LVp interval may be started upon the LA pace event. The A-LVp interval is set such that the LV is paced at an interval Z1 longer than the IACT.

If the IACT is greater than a predetermined threshold at block 306, however, a LA pacing interval is set at block 312 to shorten the delay between the RA and LA depolarizations. The LA pacing interval may be an AAI started at the onset of a far-field P-wave sensed from the LV EGM signal. An A-LVp interval is set at block 314 to be shorter than the IACT. The A-LVp interval may also be started at the onset of a far-field P-wave sensed from the LV EGM signal or may follow the LA pacing pulse.

CRT is delivered at block 316 using the CS lead 120 to pace the LA and the LV at the established time intervals while allowing the intrinsic RA rhythm to set the heart rate.

In another example, at block 312, a time interval from the LV sense and/or LV pace events to the onset of the far-field P-wave (sensed on the LV EGM signal), may be determined as an LV-RAs interval. The LAp interval may be set as an LV-LAp interval that is slightly longer than the LV-RAs interval to allow LA pacing pulses to be delivered just after the onset of the P-wave. The long IACT is corrected by delivering a LA pacing pulse earlier in the cardiac cycle than an expected intrinsic LA sense event, and the intrinsic RA rhythm is allowed to control the heart rate. The LV-LAp interval is started upon an LV sense or LV pace event such that the LA pacing pulse is delivered after the onset of the P-wave, i.e. after the start of the intrinsic RA depolarization but at a time shorter than the IACT.

The LV-RAs interval measured as the time from an LV pace or sense event to the onset of the far-field P-wave on the LV EGM signal may be re-determined periodically to update the LA pacing interval. Sensing the far-field P-wave, which may require greater processing power and signal analysis, is not required on every cardiac cycle since the LA pace interval is started from the LV events. As described below, the LA pacing interval may be adjusted periodically to examine for changes in the intrinsic RA rate to detect inadvertent overdrive pacing of the heart and reduce the likelihood of LA pacing overtaking the intrinsic RA rate.

Figure 5:
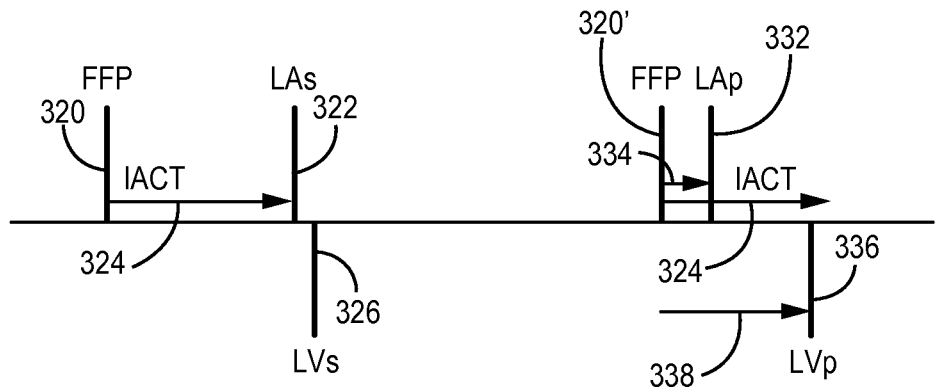
FIG. 5 is a timing diagram illustrating delivery of a pacing therapy using only pacing and sensing in the LA and the LV of the heart.

FIG. 5 is a timing diagram illustrating delivery of a pacing therapy using only pacing and sensing in the LA and the LV of the heart. The onset of a far-field P-wave (FFP) 320 is sensed from the LV EGM signal as the onset of the RA intrinsic depolarization. The LA sense event (LAs) 322 is sensed from the LA EGM signal, e.g. using electrodes 144C and 144D of quadripolar lead 120. The time interval from the FFP 320 to the LAs 322 is determined as the IACT 324. In this example, the IACT is long due to an atrial conduction disorder. The LV sense event (LVs) 326 occurs early after LAs 322, which will result in truncation of LV filling, e.g. as observed as a truncated A-wave on an echocardiographic image.

An AAI 334 is set to start upon the FFP 320' to control delivery of the LA pacing pulse (LAp) 332 to correct for the abnormally long IACT 324. An LV pacing pulse (LVp) 336 is delivered upon expiration of a RA-LVp interval 338 that is started upon sensing the FFP 320' and is shorter than the IACT 324. In this way, bi-atrial synchrony is achieved while allowing the intrinsic RA rhythm to control the heart rate, and the LV is paced at an interval that improves ventricular synchrony while maintaining optimal LA-LV timing that avoids truncation of the active LV filling phase.

Figure 6:
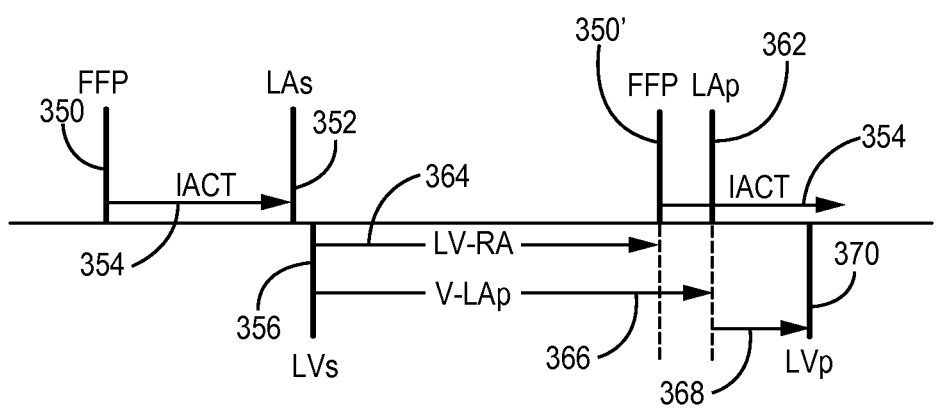
FIG. 6 is a timing diagram illustrating delivery of a pacing therapy using only pacing and sensing the LA and the LV of the heart.

FIG. 6 is a timing diagram illustrating delivery of a pacing therapy using only pacing and sensing the LA and the LV of the heart, according to another example. The FFP 350 is sensed from the LV EGM signal. The LAs 352 is sensed from the LA EGM signal and is used to measure the IACT 354. An LV-RA interval 364 is determined as the time from the LVs 356 to the next FFP 350'. Determination of the LV-RA interval 364 (which may be an average of one or more cardiac cycles) allows a V-LAp interval 366 to be set. The V-LAp interval 366, started upon each LV sense or LV pace event, is set slightly longer than the measured LV-RA interval 364. The LAp 362 is delivered upon expiration of the V-LAp interval 366. The LVp 336 is delivered upon expiration of LA-LVp interval 368 which starts upon delivery of the LAp 362 and results in a LV pacing pulse 370 being delivered earlier than the expiration of the measured IACT 354. Using this method, far-field signal analysis is performed to determine the LV-RA interval 364 on a periodic basis, e.g. once per hour, to control the LAp 362 and LVp 336 timing. As described below, variation of the timing of the LAp 362 may be performed periodically to check if the LA pacing is occurring earlier than the intrinsic RA events resulting in a LA pacing controlled heart rate.

It is recognized that in the techniques depicted in FIGS. 5 and 6, the FFP events 320 and 350 may be replaced by intrinsic RA sense events or RA pace events when a RA lead is present. The various interval measurements and pacing timing intervals that begin with the FFP events 320 or 350 may begin with an intrinsic RA sense event sensed from a RA EGM signal or a RA pacing pulse.

Figure 7:
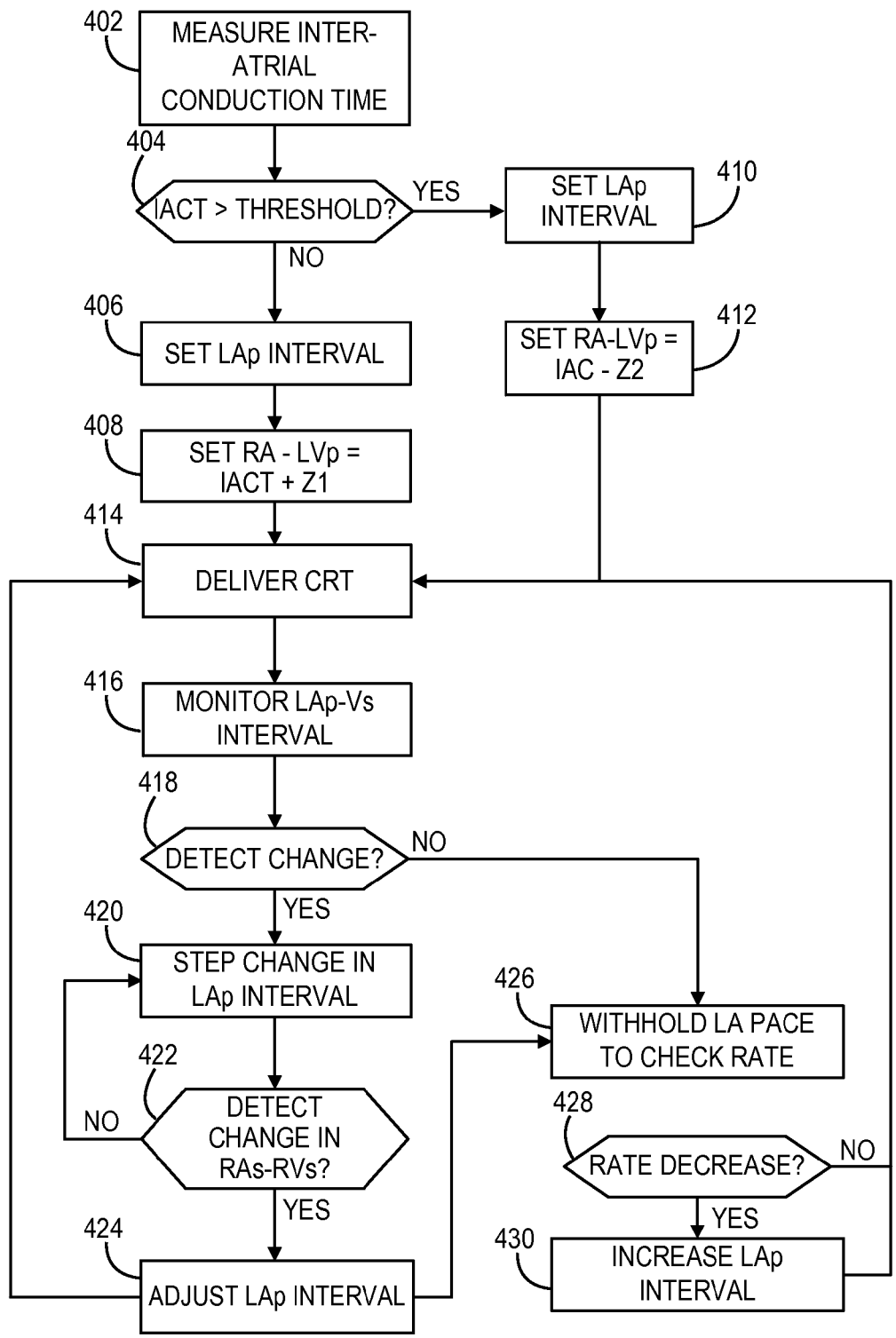
FIG. 7 is a flow chart of a method for controlling a pacing therapy according to another embodiment.

FIG. 7 is a flow chart 400 of a method for controlling a pacing therapy according to another embodiment. The IACT is measured at block 402 and the LA pacing interval and RA-LVp interval are set based upon the measured IACT at blocks 404 through 412 as described above. Intervals for controlling LA pace pulse timing and LV pacing pulse timing may be set according to the techniques depicted by the timing diagrams of FIGS. 5 and 6 in some examples. CRT is delivered using the selected intervals at block 414.

In order to promote a heart rate arising from the intrinsic RA rhythm, the LA pace to ventricular sense (LAp-Vs) interval is monitored at block 416. If a change in the RA rate occurs or if the timing of RA sense events based on far-field P-wave sensing becomes unreliable, the timing of the LA pacing pulses may lead the intrinsic RA events causing the LA pacing to usurp control of the heart rate. By monitoring the LAp-Vs interval, changes in the intrinsic RA rate and/or inadvertent overdrive pacing of the LA may be identified. The LAp-Vs interval may be a LAp-LVs or a LAp-RVs interval depending upon the available electrodes for sensing ventricular EGM signals. This monitoring may be performed on a beat-by-beat or less frequent basis.

If the LAp-Vs interval changes, as determined at block 418, the LAp timing interval is adjusted at block 420. The LAp timing interval may be an AAI started upon a FFP as described above. The LAp timing interval may alternatively be a V-LAp interval set based upon measured LVs-FFP intervals, as described above, or RVs-RAs, RVp-RAs, LVs-RAs or LVp-RAs intervals. A change in the LAp-Vsense interval may be due to a change in the intrinsic RA rate, which in turn may require an adjustment to the LA pacing interval. For example, if the intrinsic RA rate increases, the LAp-RVsense interval shortens for a given LA pacing interval. The LA pacing interval may need to be shortened in order to promote complete LA active contribution to LV filling. If the intrinsic RA rate decreases, the LAp-RVsense interval will increase for a given LA pacing interval. The LA pacing interval may need to be increased in order to promote atrial synchrony.

Figure 8A:
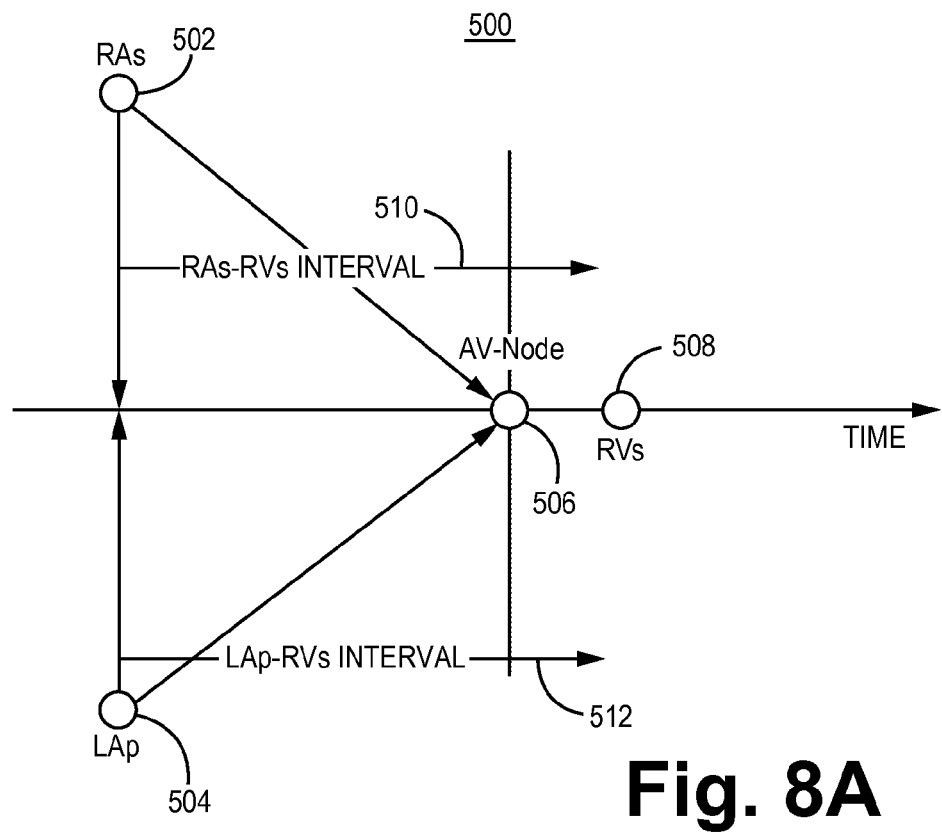
FIGS. 8A through 8C are schematic diagrams of the relative timing of right atrial, left atrial and right ventricular events that may change as the right atrial rate changes.
Figure 8B:
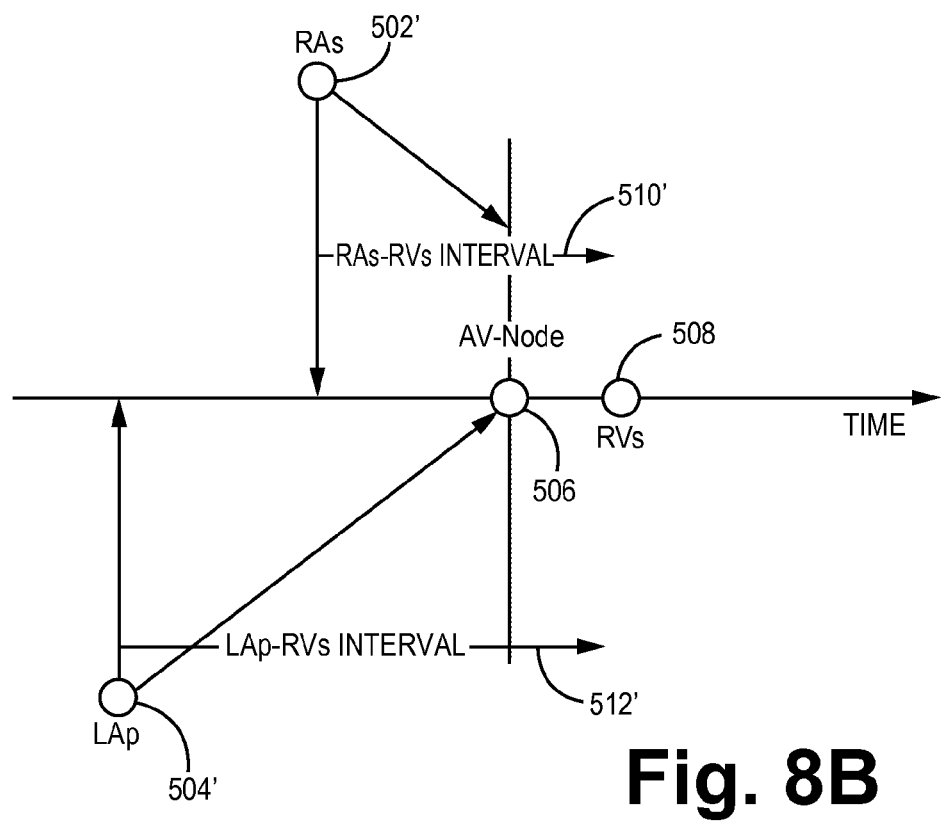
Figure 8C:
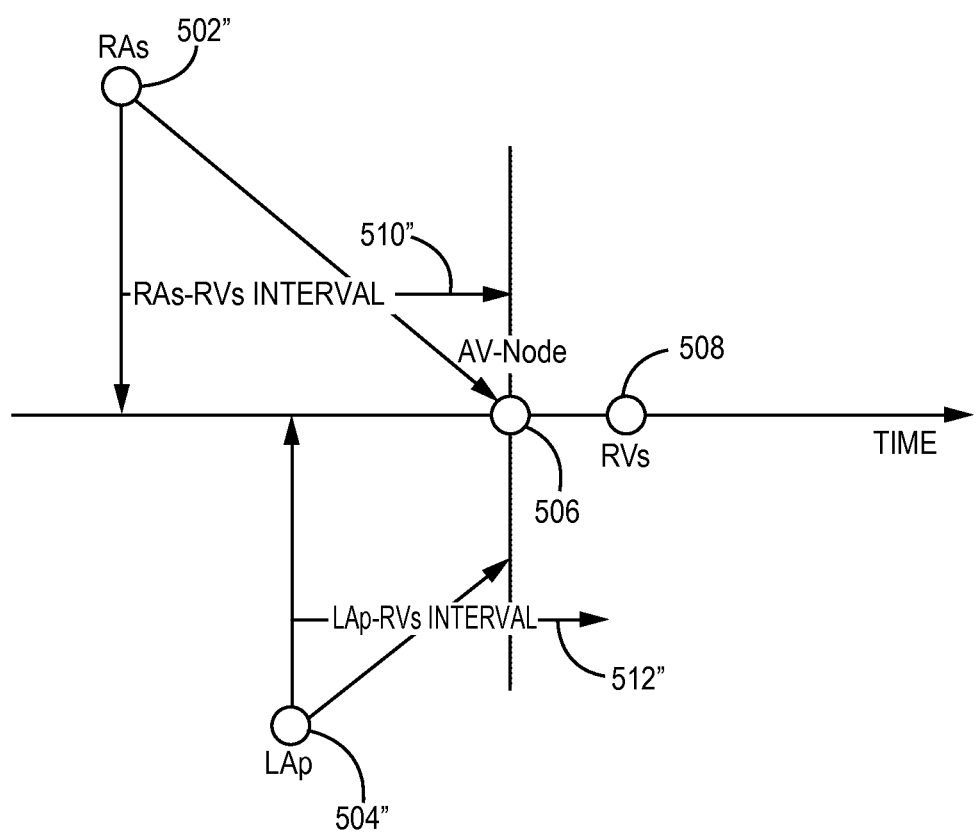

FIGS. 8A through 8C are schematic diagrams of RA, LA and RV events and relative timing that may change as the intrinsic RA rate changes. In FIG. 8A, the LA pacing pulse 504 is delivered synchronously with the intrinsic RA sense event 502 such that the two events synchronously activate the AV node 506. The synchronized atrial depolarization is conducted through the AV node 506 to the RV resulting in an RV sense event 508. The RV sense event 508 occurs at an RAs-RVs interval 510 following the RA sense event 502. The RV sense event 508 occurs at an LAs-RVs interval 512 following the LA sense event 504, which is approximately equal to the RAs-RVs interval 510 in this example due to synchronization of RAs and LVp events. In some examples, this relative timing of RA sensed events and LA paced events is desirable as long as the LA paced depolarization does not arrive at the AV-node earlier than the RA sensed event. The intrinsic RA heart rate is maintained when the LA pacing pulse is simultaneous with or slightly lags the arrival of the RA depolarization at the AV node 506.

FIG. 8B illustrates the situation of the LA pacing pulse 504' arriving at the AV node 506 earlier than an intrinsic RA sense event 502'. If the LA pacing pulse is delivered too early, the depolarization caused by the LA pacing pulse 504' will arrive at the AV node 506 earlier than the RA sense event 502', causing conduction through the AV node 506 and the subsequent depolarization of the RV (RVs 508). The timing of LA pacing in this situation will control the ventricular rhythm rather than the intrinsic RA rhythm setting the ventricular rate. Changes in the timing of the LA pacing pulse 504' relative to the RAs 502' that result in the LA depolarization conduction through the AV node 506 before the RA depolarization will result in changes in the RAs-RVs interval 512'. This situation could arise, for example, when a V-LAp interval is used to control timing of the LA pacing pulse and a change in the intrinsic RA rate occurs. Under such circumstances, further changes in the intrinsic RA rate will not cause a change in the LAp-RVs interval 512' because the LA pacing pulses are overriding the intrinsic RA activity. Changes in the LAp interval, however, will result in a change in the RAs-RVs interval 510'. If the intrinsic RA events are arriving first at the AV node 506, ahead of the pacing-evoked LA depolarization, changes in the LAp timing interval will not change the RAs-RVs interval.

Accordingly, by performing step-wise changes in the LAp timing, recognition of when the LAp 504' arrives at the AV node earlier than the RAs 502' is made based on detecting a change in the RAs-RVs interval 510'. As long as the LAp timing lags the RAs 502' at the AV node 506, LAp timing adjustments will not cause a change in the RAs-RVs interval. As soon as the LAp timing causes the pacing-evoked LA depolarization to arrive earlier at the AV node 506, the RAs-RVs time interval will change. As the timing of the LAp is adjusted from a relatively long interval to a relatively short interval, for example, the shortest LAp interval that results in no change in the RAs-RVs interval 510' when the LAp interval is increased is the shortest LAp interval that can be used without overriding the intrinsic RA rate. A LAp interval that is equal to or greater than this shortest interval may be selected to promote bi-atrial synchrony while maintaining a RA dominated heart rhythm.

FIG. 8C illustrates the situation of the depolarization arising from the LA pacing pulse 504" arriving later than the RA sense event 502" at the AV node 506. In this situation, the intrinsic RA rate is controlling the RV rate. The LAp-RVs interval 512" is relatively shorter than the RAs-RVs interval 510". If the RA rate changes, the LAp-RVs interval 512" will change even if the LAp interval is kept the same. For example, for a given V-LAp, if the RA rate increases, the RAs-RVs interval 510" will shorten causing the LAp-RAs interval 512" to shorten. If the RA rate decreases, the LAp-RVs interval 512" will lengthen up to a maximum AV conduction time as long as the intrinsic RA events arrive first at the AV node 506 and control the RV rate. Changes in the timing of the LA pacing pulse 504" will change the LAp-RVs interval 512" but will not affect the RAs-RVs interval 510" as long as the intrinsic RA depolarization is arriving at the AV node 506 first.

By monitoring for changes in the LAp-RVs interval during LA pacing, changes in RA rate can be recognized. Changes in the LAp-RVs interval for a given LAp interval will be caused by a change in the RA rate, assuming a normally conducted ventricular rhythm. If the RA rate changes, the LAp interval may need to be adjusted to promote atrial synchrony while preserving the intrinsic RA rate control of the heart rate. If a change in the LAp-RVs interval is detected, variation of the LAp interval and corresponding measurements of the RAs-RVs interval can be used to determine the earliest timing of the LAp that is synchronized with or lags behind the RA depolarization wavefront arriving at the AV node Returning to FIG. 7, at block 416, the LAp-Vs interval is monitored to detect a change in the interval during LA pacing. For example the current LAp-RVs interval may be compared to one or more previous LAp-RVs intervals, a trend in the intervals may be determined, or other comparative analysis may be performed to detect a change in the LAp-RVs interval that may be indicative of a change in the intrinsic RA rate. If a change is detected, the LAp interval is adjusted to a number of different pacing intervals, e.g. in a stepwise manner, to determine if a change in RAs-RVs interval occurs. If the RA rate is controlling the RV rate, step changes in the LAp interval should cause changes in the LAp-RVs interval without changing the RAs-RVs interval. If no change in the RAs-RVs interval occurs (but a change in the LAp-RVs interval does occur), the arrival of the LA paced depolarization lags the arrival of RA intrinsic depolarization at the AV node. CRT delivery may continue at the existing settings or further step changes to the LAp interval may be performed until a change in the RAs-RVs interval does occur, as determined at block 422.

Once the RAs-RVs interval does change as the LAp interval is adjusted, the LA pacing has overtaken the atrial rate and is controlling the ventricular rate. The LAp interval can be adjusted at block 424 until the RA rate is controlling the ventricular rate again. For example, the LAp interval may be increased just until a step change in LA pacing pulse timing does not cause a change in the RAs-RVs interval. At this point, the LA depolarization arising from the LA pacing pulse is synchronized with or slightly lags the intrinsic RA depolarization arrival at the AV node.

As long as the LA-RVs interval does change with small step changes in the LA pacing interval timing, and no change in the RAs-RVs interval occurs, the LA pacing pulse is being delivered within the RA-RV conduction time with the intrinsic RA rate still controlling the ventricular rate.

Periodically, the RA rate may be checked by withholding the LA pacing at block 426. In one example, LA pacing is withheld for one or more cardiac cycles once per minute. If the RA rate, or the RV rate, decreases as determined at block 428, the LA pacing had been controlling the ventricular rate. The AAI (or VA interval) is adjusted at block 430 to promote intrinsic heart rate control by the RA with the LA pacing pulse slightly lagging the RA sensed event.

Figure 9A:
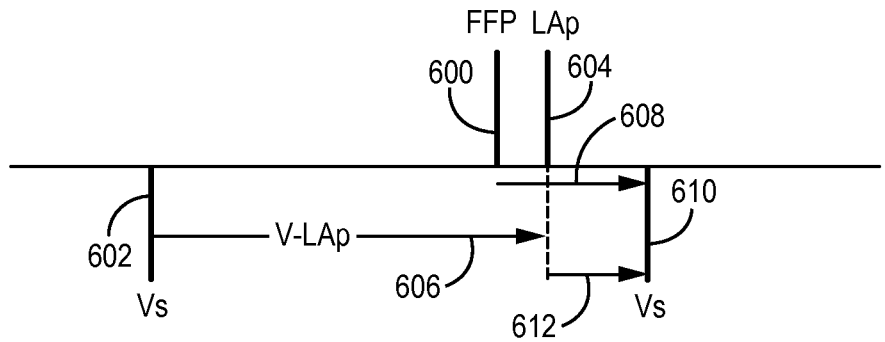
FIGS. 9A-9C are timing diagrams illustrating techniques performed in the flow chart of FIG. 7.
Figure 9B:
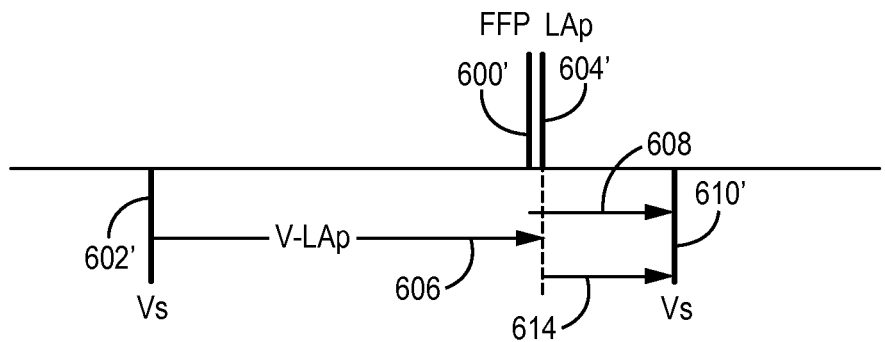
Figure 9C:
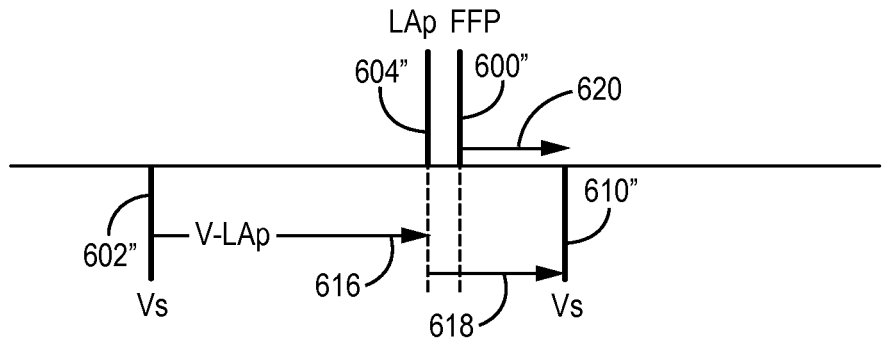

FIGS. 9A-9C are timing diagrams illustrating techniques performed in the flow chart of FIG. 7. In FIG. 9A, FFP 600 is the onset of a far-field P-wave sensed from a LV EGM signal as a substitute for sensing RA P-waves directly when RA sense electrodes are unavailable, for example in a system that does not include a RA lead. Vs 602 is a ventricular sensed event, e.g. a LV sense event. The LAp 604 is delivered at a V-LAp interval 606 and lags the intrinsic RA depolarization as represented by FFP 600. A subsequently sensed ventricular event Vs 610 follows FFP 600 by an AV conduction interval shown by RAs-Vs interval 608. LAp 604 occurs at an LAp-Vs interval 612 prior to Vs 610. This LAp-Vs interval 612 may be monitored at block 416 of FIG. 7 to detect changes in the intrinsic RA rate and/or inadvertent overdrive pacing of the atria.

If FIG. 9B, the intrinsic RA rate has decreased as compared to the situation of FIG. 9A resulting in the FFP 600' occurring relatively later following VS 602'. The LAp 604' is delivered at the currently programmed V-LAp interval 606. Vs 610' occurs at the AV conduction interval (interval 608) following the FFP 600'. The LAp-Vs interval 614, however, has increased compared to the LAp-Vs interval 612 in FIG. 9A because the LAp 604' is delivered relatively earlier in the AV conduction time interval 608. The intrinsic RA rate is still controlling the heart rate, but the change in the LAp-Vs interval 614 indicates that a change in the heart rate has occurred. This change in heart rate can be detected by monitoring the LAp-Vs interval 612, 614 periodically without having to sense the RA intrinsic events.

To verify that this detected change in intrinsic heart rate has not resulted in LA overdrive pacing, the LAp interval may be shortened and/or increased in a step-wise manner until changes in the LAp interval cause a change in the RAs-Vs interval 608. In FIG. 9C, the V-LAp interval 616 following a Vs event 602" is intentionally shortened and results in the LAp 604" leading the intrinsic RA sense event represented by FFP 600". The LAp-Vs interval 618 is now longer than the FFP-Vs interval 620. The LAp-VS interval 618 is equal to the AV conduction time represented by RAs-Vs intervals 608 in FIGS. 9A and 9B because the LAp evokes a depolarization wavefront arriving at the AV node earlier than the intrinsic RA event. The LAp evoked response is conducted through the AV node to cause the Vs event 610". The RAs-Vs interval 620 (measured from the FFP onset 600") is shorter than the AV conduction time. The relatively short LAp interval 616 results in overdrive pacing of the atria. Further decreases in the V-LAp interval 616 will result in further decreases in the FFP-Vs interval 620. The change in the LAp-Vs interval 614 and the change in FFP-Vs interval 620 after shortening the V-LAp interval 616 indicate that the intrinsic RA rate has changed, but that the V-LAp interval 606 (shown in FIG. 9B) can still be used without overdrive pacing the intrinsic RA rhythm. The shortest LAp interval can be identified that, when further increased, does not cause a change in the RAs-Vs interval 618. This shortest LAp interval is the earliest timing of the LAp that does not overdrive pace the atria but provides improved bi-atrial synchrony.

Thus, various embodiments of a system and method for controlling a cardiac pacing therapy have been described. One of ordinary skill in the art will appreciate that various modifications may be made to the described embodiments without departing from the scope of the claims. The examples presented herein may be modified, for example by re-ordering various steps or combining or omitting disclosed steps to arrive at other combinations than depicted in the illustrative flow charts presented herein. These and other examples are within the scope of the following claims.

The invention claimed is:

1. An automated method for controlling a cardiac pacing therapy, comprising:
    determining by a processor an inter-atrial conduction time (IACT);
    comparing the IACT to a threshold;
    setting a pacing interval for controlling delivery of pacing pulses to a ventricle to a first ventricular pacing interval that expires after the IACT in response to the IACT being less than the threshold; and
    setting the pacing interval to a second ventricular pacing interval that expires before the IACT in response to the IACT being greater than the threshold.

2. The method of claim 1, further comprising, setting a left atrial pacing interval to pace the left atrium earlier than an expiration of the IACT.

3. The method of claim 2, further comprising:
    setting a left atrial pacing interval to a first left atrial pacing interval that expires earlier than the expiration of the IACT in response to the IACT being less than the threshold;
    setting the left atrial pacing interval to a second left atrial pacing interval that expires earlier than the IACT in response to the IACT being greater than the threshold,
    the first left atrial pacing interval being a first value less than the IACT,
    the second left atrial pacing interval being a second value less than the IACT, the second value being greater than the first value.

4. The method of claim 2, further comprising:
    delivering left atrial pacing at the left atrial pacing interval;
    withholding the left atrial pacing;
    determining a right atrial rate during each of the left atrial pacing and during the withholding; and
    adjusting the left atrial pacing interval if the right atrial rate is slower during the withholding than during the left atrial pacing.

5. The method of claim 4, wherein determining the right atrial rate comprises determining an onset of a far-field P-wave from a ventricular electrogram signal.

6. The method of claim 2, further comprising:
    delivering left atrial pacing at the left atrial pacing interval;
    monitoring a time interval between a left atrial pacing pulse and a sensed ventricular event;
    determining that a change in the right atrial rate has occurred in response to detecting a change in the monitored time interval; and
    adjusting the left atrial pacing interval in response to determining that the change in the right atrial rate has occurred.

7. The method of claim 1, further comprising:
    delivering left atrial pacing at an initial left atrial pacing interval;
    monitoring a time interval between a left atrial pacing pulse and a sensed ventricular event during the left atrial pacing;
    responsive to a change in the monitored time interval; delivering the left atrial pacing at a plurality of different left atrial pacing intervals;
    determining a time interval between a sensed right atrial event and a sensed ventricular event for each of the plurality of different left atrial pacing intervals;
    determining a shortest interval of the plurality of left atrial pacing intervals from which an increase in the left atrial pacing interval does not cause a change in the time interval between the sensed right atrial event and the sensed ventricular event; and
    setting the left atrial pacing interval to an adjusted interval that is at least equal to the shortest interval.

8. The method of claim 7, further comprising:
    determining an LV-RA time interval between a left ventricular event and right atrial event;
    setting the initial left atrial pacing interval in response to the LV-RA time interval;
    wherein at least one of determining the LV-RA time interval and determining the time interval between the right atrial events and the sensed ventricular events for each of the plurality of different left atrial pacing intervals comprises determining an onset of a far-field P-wave from a ventricular electrogram signal.

9. The method of claim 1, further comprising:
    delivering left atrial pacing pulses earlier than an expiration of the IACT;

monitoring a time interval between the left atrial pacing pulses and respective sensed right ventricular events; and adjusting a left atrial pacing interval used for delivering the left atrial pacing pulses in response to a change in the monitored time interval.

10. The method of claim 1, further comprising:
sensing cardiac signals from a plurality of electrodes positioned only along a coronary sinus lead; and
determining the IACT solely from the sensed cardiac signals.

11. A medical device for delivering a cardiac pacing therapy, comprising:
a sensing module configured to sense cardiac signals;
a therapy delivery module configured to deliver cardiac pacing pulses;
a controller coupled to the sensing module and the therapy delivery module and configured to:
determine an inter-atrial conduction time (IACT);
compare the IACT to a threshold;
set a pacing interval for controlling delivery of pacing pulses to a ventricle to a first ventricular pacing interval that expires after the IACT in response to the IACT being less than the threshold; and
set the pacing interval to a second ventricular pacing interval that expires before the IACT in response to the IACT being greater than the threshold.

12. The device of claim 11, wherein the controller is further configured to set a left atrial pacing interval to pace the left atrium earlier than an expiration of the IACT.

13. The device of claim 11, wherein the controller is further configured to:
setting a left atrial pacing interval to a first left atrial pacing interval that expires earlier than the expiration of the IACT in response to the IACT being less than the threshold;
setting the left atrial pacing interval to a second left atrial pacing interval that expires earlier than the IACT in response to the IACT being greater than the threshold,
the first left atrial pacing interval being a first value less than the IACT,
the second left atrial pacing interval being a second value less than the IACT, the second value being greater than the first value.

14. The device of claim 12, wherein the controller is further configured to:
control the therapy delivery module to deliver left atrial pacing at the left atrial pacing interval;
withhold the left atrial pacing;
determine a right atrial rate during each of the left atrial pacing and during the withholding; and
adjust the left atrial pacing interval if the right atrial rate is slower during the withholding than during the left atrial pacing.

15. The device of claim 14, wherein determining the right atrial rate comprises determining an onset of a far-field P-wave from a ventricular electrogram signal sensed by the sensing module.

16. The device of claim 12, wherein the controller is further configured to:
control the therapy delivery module to deliver left atrial pacing at the left atrial pacing interval;
monitor a time interval between a left atrial pacing pulse and a sensed ventricular event;
determine that a change in the right atrial rate has occurred in response to detecting a change in the monitored time interval; and adjust the left atrial pacing interval in response to determining that the change in the right atrial rate has occurred.

17. The device of claim 11, wherein the controller is further configured to:
control the therapy delivery module to deliver left atrial pacing at an initial left atrial pacing interval;
monitor a time interval between a left atrial pacing pulse and a sensed ventricular event during the left atrial pacing;
responsive to a change in the monitored time interval, control the therapy delivery module to deliver the left atrial pacing at a plurality of different left atrial pacing intervals;
determine a time interval between a sensed right atrial event and a sensed ventricular event for each of the plurality of different left atrial pacing intervals;
determine a shortest interval of the plurality of left atrial pacing intervals from which an increase in the left atrial pacing interval does not cause a change in the time interval between the sensed right atrial event and the sensed ventricular event; and
set the left atrial pacing interval to an adjusted interval that is at least equal to the shortest interval.

18. The device of claim 17, wherein the controller is further configured to:
determine an LV-RA time interval between a left ventricular event and right atrial event; and
set the initial left atrial pacing interval in response to the LV-RA time interval;
wherein at least one of determining the LV-RA time interval and determining the time interval between the right atrial events and the sensed ventricular events for each of the plurality of different left atrial pacing intervals comprises determining an onset of a far-field P-wave from a ventricular electrogram signal.

19. The device of claim 11, wherein the controller is further configured to:
control the therapy control module to deliver left atrial pacing pulses earlier than an expiration of the IACT;
monitor a time interval between the left atrial pacing pulses and respective sensed right ventricular events; and
adjust a left atrial pacing interval used for delivering the left atrial pacing pulses in response to a change in the monitored time interval.

20. The device of claim 11, wherein the sensing module is configured to sense cardiac signals from a plurality of electrodes positioned only along a coronary sinus lead; and
the controller is configured to determine the IACT solely from the sensed cardiac signals.

21. A non-transitory, computer-readable storage medium storing instructions for causing a medical device to:
determine an inter-atrial conduction time (IACT);
compare the IACT to a threshold;
set a pacing interval for controlling delivery of pacing pulses to a ventricle to a first ventricular pacing interval that expires after the IACT in response to the IACT being less than the threshold; and
set the pacing interval to a second ventricular pacing interval that expires before the IACT in response to the IACT being greater than the threshold.

22. A medical device for delivering a cardiac pacing therapy, comprising:
sensing means for sensing cardiac signals;
processing means for determining an inter-atrial conduction time (IACT) from the sensed cardiac signals and comparing the IACT to a threshold; and control means for:
- setting a pacing interval for controlling delivery of pacing pulses to a ventricle to a first ventricular pacing interval that expires after the IACT in response to the IACT being less than the threshold; and
- setting the pacing interval to a second ventricular pacing interval that expires before the IACT in response to the IACT being greater than the threshold.

* * * * *